US010172829B2

(12) United States Patent
Bender et al.

(10) Patent No.: US 10,172,829 B2
(45) Date of Patent: Jan. 8, 2019

(54) USE OF SMALL MOLECULES FOR THE TREATMENT OF CLOSTRIDIUM DIFFICILE TOXICITY

(71) Applicant: The Board of Trustees of the Leland Stanford Junior University, Stanford, CA (US)

(72) Inventors: Kristina Oresic Bender, Redwood City, CA (US); Aaron Puri, Seattle, WA (US); Aimee Shen, Cambridge, MA (US); Matthew S. Bogyo, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/319,358

(22) PCT Filed: Jun. 23, 2015

(86) PCT No.: PCT/US2015/037242
§ 371 (c)(1),
(2) Date: Dec. 15, 2016

(87) PCT Pub. No.: WO2015/200358
PCT Pub. Date: Dec. 30, 2015

(65) Prior Publication Data
US 2017/0128420 A1 May 11, 2017

Related U.S. Application Data

(60) Provisional application No. 62/016,420, filed on Jun. 24, 2014.

(51) Int. Cl.
| | | |
|---|---|---|
| *A61K 31/41* | (2006.01) | |
| *A61K 31/167* | (2006.01) | |
| *A61K 31/4365* | (2006.01) | |
| *A61K 31/555* | (2006.01) | |
| *A61K 9/50* | (2006.01) | |
| *A61K 31/437* | (2006.01) | |
| *A61K 31/496* | (2006.01) | |
| *C12Q 1/04* | (2006.01) | |
| *A61K 9/16* | (2006.01) | |
| *A61K 9/28* | (2006.01) | |

(52) U.S. Cl.
CPC ............ *A61K 31/41* (2013.01); *A61K 9/5026* (2013.01); *A61K 31/167* (2013.01); *A61K 31/437* (2013.01); *A61K 31/4365* (2013.01); *A61K 31/496* (2013.01); *A61K 31/555* (2013.01); *C12Q 1/04* (2013.01); *A61K 9/1635* (2013.01); *A61K 9/1652* (2013.01); *A61K 9/2846* (2013.01)

(58) Field of Classification Search
None
See application file for complete search history.

(56) References Cited

U.S. PATENT DOCUMENTS

| | | | |
|---|---|---|---|
| 4,711,961 A | 12/1987 | Welter et al. | |
| 8,372,869 B2 | 2/2013 | Billack et al. | |
| 8,592,468 B2 | 11/2013 | Holmgren et al. | |
| 2004/0106590 A1 | 6/2004 | Eisenstein | |
| 2004/0142035 A1 | 7/2004 | Chang et al. | |
| 2009/0005422 A1 | 1/2009 | Holmgren et al. | |
| 2010/0227899 A1* | 9/2010 | Billack ............... | A61K 31/095 514/359 |
| 2010/0239682 A1* | 9/2010 | Andremont .......... | A61K 9/1652 424/497 |
| 2011/0178002 A1 | 7/2011 | Dieckgraefe | |
| 2013/0224259 A1 | 8/2013 | Ghebremariam et al. | |
| 2014/0088149 A1 | 3/2014 | Holmgren et al. | |

FOREIGN PATENT DOCUMENTS

| | | |
|---|---|---|
| WO | 2006096759 | 9/2006 |
| WO | 2009037264 | 3/2009 |

OTHER PUBLICATIONS

Chourasia, M.K. et al., "Pharmaceutical approaches to colon targeted drug delivery systems," J Pharm Sci. (Jan.-Apr. 2003) 6(1):33-66.
Farrow, M.A. et al., "Clostridium difficile toxin B-induced necrosis is mediated by the host epithelial cell NADPH oxidase complex," Proc. Natl. Acad. Sci. U.S.A. (2013) 110:18674-18679.
Favrot, L. et al., "Mechanism of inhibition of *Mycobacterium tuberculosis* antigen 85 by ebselen," Nat. Commun. (2013)4:2748.
He, D. et al., "Clostrdium difficile Toxin A Triggers Human Coloncyte IL-8 Release via Mitochondrial Oxygen Radical Generation," Gastroenterology (2002) 122:1048-1057.
Lanis, J.M. et al., "Variations in TcdB Activity and the Hypervirulence of Emerging Strains of Clostridium difficile," PLoS Pathog. (Aug. 2010) 6(8):e1001061.
Lieberman, O. J. et al., "High-throughput screening using the differential radial capillary action of ligand assay identifies ebselen as an inhibitor of diguanylate cyclases," ACS Chem. Biol. (2014) 9:183-192.
Puri, A.W. et al., "Rational design of inhibitors and activity-based probes targeting Clostridium difficile virulence factor TcdB," Chem Biol. (Nov. 24, 2010) 17(11):1201-11.

(Continued)

*Primary Examiner* — Jake M Vu
(74) *Attorney, Agent, or Firm* — Brian E. Davy; Bozicevic, Field & Francis LLP

(57) ABSTRACT

Disclosed are methods and compositions for reducing toxicity associated with infection by *Clostridium difficile* by inhibiting *Clostridium difficile* toxin B (TcdB) and/or toxin A (TcdA). Such compounds include ebselen compounds, namely ebselen and its salts, ebselen functional analogues and ebselen structural analogues, as well as certain amide derivatives. This includes Formula I, e.g. 1-methyl-3-phenylpropylamine, Formula II, e.g., 2,2'-diselane-1,2-diylbis [N-(2,4-difluorophenyl)benzamide]; and Formula III, e.g. 2-(2-methoxy-5-methylphenyl)-1,2-benzoselenazol-3-one.
The present compositions may be comprised in a colon-retentive formulation that increases residence of and/or release of the compound in the area where the infection is active.

9 Claims, 8 Drawing Sheets

(56) References Cited

OTHER PUBLICATIONS

Zhao, R. et al., "A Novel Antioxidant Mechanism of Ebselen Involving Ebselen Diselenide, a Substrate of Mammalian Thioredoxin and Thioredoxin Reductase," The Journal of Biological Chemistry (Oct. 18, 2002) 277:39456-39462.
Dimmeler (Ebselen prevents inositol (1,4,5)-trisphosphate biding to its receptor Biochemical Pharma. (1991) 42(5):1151-1153.
Nozawa et al. "Susceptibility of Methicillin-Resistant *Staphylococcus aureus* to the Selenium-Containing Compound 2-Phenyl-1,2-Benzoisoselenazol-3(2H)-One (PZ51)" Antimicrobial Agents and Chemotherapy, (1989) 33(8):1388-1390.
Parnham and Sies "The early research and development of ebselen" Biochem. Pharma. (2013) 86:1248-1253.
Pietka-Ottlik et al. (2008) "New Organoselenium Compounds Active against Pathogenic Bacteria, Fungi and Viruses" Chem. Pharm. Bull., 56(10)1423-1427.

* cited by examiner

USE OF SMALL MOLECULES FOR THE TREATMENT OF CLOSTRIDIUM DIFFICILE TOXICITY

CROSS-REFERENCE TO RELATED APPLICATIONS

This application claims priority from U.S. Provisional Patent Application No. 62/016,420, filed 24 Jun. 2014, which is hereby incorporated by reference in its entirety, and is a U.S. national stage application of PCT/US2015/037242, having an international filing date of 23 Jun. 2015, the disclosure of which is incorporated herein by reference in its entirety.

STATEMENT OF GOVERNMENTAL SUPPORT

None.

REFERENCE TO SEQUENCE LISTING, COMPUTER PROGRAM, OR COMPACT DISK

None.

BACKGROUND OF THE INVENTION

Field of the Invention

The present invention relates to the field of infectious disease, in particular to therapeutics for the treatment of *Clostridium difficile* infection.

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

*Clostridium difficile* infection (CDI) is worldwide health threat that is typically triggered by the use of broad-spectrum antibiotics, which disrupt the natural microbial gut flora and allow the Gram-positive anaerobic pathogen to thrive. The increased incidence and severity of the disease coupled with decreased response, high recurrence rates, and emergence of multiple antibiotic resistant bacteria has created an urgent need for new therapies[1]. Here we describe targeting the cysteine protease domain (CPD) of the *C. difficile* major virulence factor toxin B (TcdB) that is critical for the pathophysiological function of the toxin within host cells. Using an activity-based probe for the toxin CPD[2], we performed a high-throughput fluorescence polarization screen and identified a number of potent inhibitors, including one bioactive compound, ebselen, which is currently in use in human clinical trials for other indications. This drug showed activity in biochemical and cell-based studies. Most importantly, treatment of a mouse model of CDI that closely resembles the human infection[3] confirmed a significant therapeutic benefit in the form of reduced disease pathology in host tissues. Our results confirm that a non-antibiotic drug that blocks function of a major bacterial virulence factor can modulate the histopathology of disease and therefore should immediately be explored as a potential therapeutic for the treatment of CDI.

CDI is the leading cause of nosocomial diarrhea and the sole cause of pseudomembrane colitis[4]. With a yearly average of over a quarter million hospitalizations in the US[5], this infectious disease places a burden of over $1 billion on the US health care system[6]. Furthermore, the mortality rate in patients with CDI is high: 6.9% at 30 days after diagnosis and 16.7% at 1 year[7]. Skyrocketing numbers of cases in the past decade (139,000 in 2002 versus 336,600 in 2012), increasing recurrence, and a rise in the number of strains resistant to almost all available antibiotics is creating a significant public health threat[8]. Only a handful of options are available to treat CDI infection, antibiotics being the main clinical practice. Recurrence rates for CDI are as high as 25%, with most patients returning to the clinic for antibiotic treatment as soon as diarrhea recurs[9,10]. By disrupting the growth cycle of bacteria, antibiotics rapidly select for resistant subpopulations[11]. As such, the rates of nosocomial antibiotic-resistant opportunistic pathogens causing infections have more than doubled in the past decade[12,13]. Although fecal bacteriotherapy has proven to be a highly effective treatment for CDI patients[14], it remains controversial from the aspect of drug regulation with the long-term effects on human health remaining uncharacterized[15].

An important potential strategy to combat bacterial pathogens is to block the ability of bacteria to harm the host by inhibiting bacterial virulence factors[16]. This strategy would help limit antibiotic use and in turn decrease the rate of emergence of resistant strains. In contrast to antibiotic treatment, targeting virulence factors may help to promote regrowth of the commensal gut flora, a key factor in mediating resistance to CDI[17]. The pathology of CDI is mediated exclusively by large clostridial toxins (TcdA and B) and only toxigenic *C. difficile* causes disease[18,19]. All disease-causing strains, including the epidemic BI/NAP1/027[20], carry the gene for toxin B[21]. The toxin is comprised of a putative receptor binding domain, a transmembrane domain, a CPD, and a glucosyltransferase domain (GTD)[22]. When endocytosed, and upon acidification within vesicles, it undergoes membrane translocation, exposing the CPD to the mammalian-specific cytosolic sugar, 1D-myo-inositol hexakisphosphate (IP6)[23]. The allosteric binding of IP6 activates the CPD to autocatalytically cleave the GTD domain which induces toxicity by irreversible glucosylation of the Rho-Rac family of small GTPases in host intestinal epithelial cells. This event results in rearrangement of the actin cytoskeleton, acute inflammation, massive fluid secretion, and finally necrosis of the mucosal layer[24, 25] causing symptoms such as severe diarrhea, fever, nausea, abdominal pain/tenderness, and loss of appetite[26]. Severe cases of CDI are characterized by pseudomembranous colitis; perforations of the colon; and sepsis[27], and in acute situations, the mortality rate can be as high as 40%. Even though the pathology of CDI is mediated by toxins, none of the currently available treatments target these major virulence factors.

Specific Patents and Publications

Puri et al., "Rational design of inhibitors and activity-based probes targeting *Clostridium difficile* virulence factor TcdB," Chem Biol. 2010 Nov. 24; 17(11):1201-11, discloses the rational design of covalent small molecule inhibitors of TcdB CPD and the identification of compounds that inactivate TcdB holotoxin function in cells. Such peptides do not contain an alpha-beta unsaturated structure.

Zhao et al., "A Novel Antioxidant Mechanism of Ebselen Involving Ebselen Diselenide, a Substrate of Mammalian Thioredoxin and Thioredoxin Reductase," Oct. 18, 2002 The Journal of Biological Chemistry, 277, 39456-39462, discloses the following reaction and dimer compound:

The paper discloses that the above reaction occurs when ebselen reacts with its selenol forming an ebselen diselenide. This compound is, as indicated in the title of the paper, is a substrate of mammalian thioredoxin and thioredoxin reductase; the authors propose a novel mechanism for ebselen antioxidant activity. This antioxidant activity is disclosed as important to ebselen's neuroprotective effects.

BRIEF SUMMARY OF THE INVENTION

The following brief summary is not intended to include all features and aspects of the present invention, nor does it imply that the invention must include all features and aspects discussed in this summary.

The present invention comprises, in certain embodiments, methods of inhibiting toxicity of Clostridium difficile toxins and/or resulting toxicity, comprising contacting such a toxin in a subject, with a composition comprising an effective amount of an ebselen-related compound as described below.

The present invention comprises, in certain embodiments, carrying out methods as described above in a subject in need thereof, wherein the composition further comprises a colon-retentive formulation. The method may further comprise administering to a subject in need an antibiotic used to treat C. difficile infection, namely at least one of metronidazole (Flagyl), Dificid (fidaxomicin), or vancomycin (Vancocin).

The present invention comprises, in certain embodiments, a pharmaceutical composition for treating Clostridium difficile toxicity, comprising an ebselen-related compound in an oral formulation for release in the colon, at a pH between 6.0 and 7.0. In certain embodiments, the composition comprises or consists essentially of an ebselen-related as described below. In certain embodiments, the composition comprises an ebselen-related compound selected from the group consisting of ebselen, an ebselen salt, and an ebselen structural analogue as listed below. The present invention comprises, in certain embodiments, a pharmaceutical composition that comprises two or more enteric materials surrounding a core of an ebselen-related compound.

In certain embodiments, the composition comprises a pharmaceutical composition as described above, wherein the ebselen-related compound is prepared as a prodrug that is converted into an active compound in the colon. In certain embodiments, the composition comprises a pharmaceutical composition entrapped into chitosan cores and Eudragit S100/Eudragit L100 coatings, i.e. anionic copolymers based on methacrylic acid and methyl methacrylate.

The present invention comprises, in certain embodiments, a method for ameliorating toxicity arising from a Clostridium difficile infection in a subject, comprising the step of administering to said subject an oral pharmaceutical composition having a single ingredient, wherein the active ingredient is ebselen, an ebselen structural analogue, or an ebselen functional analogue. In certain embodiments of the present methods, the subject exhibits pseudomembranous colitis, perforations of the colon, or sepsis.

In certain embodiments, the invention comprises a method of inhibiting toxicity of Clostridium difficile toxin B (TcdB) comprising contacting TcdB with a composition described herein. Also, the invention comprises contacting Clostridium difficile toxin A (TcdA) with a composition described herein. The method of the invention comprises contacting the presently described compositions with TcdB, TcdA, or both. It further comprises in vitro assays comprising contacting compositions as described herein and measuring their effect on the protease domain of TcdB, TcdA, or both.

In certain embodiments, the invention comprises a method of inhibiting a Clostridium difficile toxin which is at least one of TcdB and TcdA, comprising the step of contacting said toxin with a composition comprising an effective amount of an ebselen composition and thereby inhibiting enzymatic activity of said toxin.

In certain embodiments, the invention comprises method of inhibiting a Clostridium difficile toxin which is at least one of TcdB and TcdA, comprising the step of contacting said toxin with a pharmaceutical composition comprising an effective amount of a compound according to at least one of (a)

Formula I wherein R is aryl alkylamine, piperazine substituted with carboxylate ester, cycloalkylsulfanyl alkylamine, aryl alkylamine with a halogen-substituted aryl, alkylamine, alkoxy alkylamine, or benzodioxolyl alkylamine;

(b)

Formula II wherein $R_1$, $R_2$, $R_3$, and $R_4$ are each independently selected from the group consisting of —F, —OCH$_3$, —H, —Cl, and —CH$_3$;

and (c),

Formula III wherein $R_5$ and $R_6$ are each independently selected from the group consisting of —OH, —H, —CH$_3$, —OCH$_3$, —Cl, and -t-butyl, and X is selected from the group consisting of C and N; and thereby inhibiting enzymatic activity of a present toxin.

In certain embodiments, the invention comprises a method for inhibiting Tcdb or TcdA in a pharmaceutical composition, wherein the compound is of Formula I:

Formula I and, wherein R is selected from the group consisting of 1-methyl-3-phenylpropylamine, methyl piperazine-1-carboxylate, 3-(cyclohexylsulfanyl)propylamine, 2-(4-chlorophenyl)ethylamine, butylamine, 3-ethoxypropylamine, 2-methoxyethylamine, and 1,3-benzodioxol-5-ylmethylamine.

In certain embodiments, the invention comprises a method for inhibiting Tcdb or TcdA in a pharmaceutical composition wherein the compound is of Formula II:

Formula II and, wherein
(a) $R_1$, $R_2$, $R_3$, and R4 are each —F bonded to positions 2 and 4;
(b) $R_1$ and R3 are each —OCH$_3$ bonded to position 3, and $R_2$ and R4 are each —H;
(c) $R_1$ and R3 are each —Cl bonded to position 2, and $R_2$ and R4 are each —CH$_3$ bonded to position 4;
(d) $R_1$ and R3 are each —Cl bonded to position 2, and $R_2$ and R4 are each —F bonded to position 6;
(e) $R_1$ and R3 are each —F bonded to position 2, and $R_2$ and R4 are each —H;
(f) $R_1$ and R3 are each —Cl bonded to position 3, and R2 and R4 are each —F bonded to position 4;
(g) $R_1$ and R3 are each —Cl bonded to position 3, and $R_2$ and R4 are each —CH$_3$ bonded to position 2;
(h) $R_1$ and R3 are each —Cl bonded to position 2, and $R_2$ and R4 are each —CH$_3$ bonded to position 5;
(i) $R_1$ and R3 are each —Cl bonded to position 2, and $R_2$ and R4 are each —F bonded to position 4; or
(j) $R_1$ and R3 are each —Cl bonded to position 5, and $R_2$ and R4 are each —OCH$_3$ bonded to position 2.

In certain embodiments, the invention comprises a method for inhibiting Tcdb or TcdA using a compound in a pharmaceutical composition comprising the compound is of Formula III:

Formula III and, wherein
(a) R5 is —OH bonded to position 2, $R_6$ is —H, and X is C;
(b) R5 is —CH$_3$ bonded to position 4, $R_6$ is —H, and X is C;
(c) R5 is —OCH$_3$ bonded to position 2, $R_6$ is —CH$_3$ bonded to position 5, and X is C;
(d) R5 is —OCH$_3$ bonded to position 4, $R_6$ is —CH$_3$ bonded to position 2, and X is C;
(e) R5 is —Cl bonded to position 4, $R_6$ is —F bonded to position 2, and X is C;
(f) R5 is —OH bonded to position 2, $R_6$ is —H, and X is N; or
(g) R5 is —OCH$_3$ bonded to position 2, $R_6$ is -t-butyl bonded to position 5, and X is C.

In certain embodiments, the invention comprises a method for inhibiting Tcdb or TcdA using a compound as described above, carried out in a subject having a *Clostridium difficile* infection, and wherein the composition further comprises a colon-retentive formulation. In certain embodiments, the invention comprises the steps of testing a subject for the presence of a *Clostridium difficile* infection and administering a recited composition if testing shows *Clostridium difficile* infection.

In certain embodiments, the invention comprises methods as described above wherein the step of inhibiting a *Clostridium difficile* toxin comprises administering a recited composition to a subject identified as one who exhibits pseudomembranous colitis, perforations of the colon, or sepsis. In certain embodiments, the invention comprises the above-described method for inhibiting a *Clostridium difficile* toxin further comprising the step of administering to a subject suffering *Clostridium difficile* infection at least one of metronidazole, fidaxomicin, or vancomycin.

In certain embodiments, the invention comprises a pharmaceutical composition comprising compounds as described above in connection with Formula I, Formula II, or Formula III. In certain embodiments, the composition is in an oral formulation for release in the colon, and for release at a pH between 6.0 and 7.0. In certain embodiments, the composition comprises a compound is entrapped into chitosan cores and Eudragit S100/Eudragit L100 coatings, i.e. anionic copolymers based on methacrylic acid and methyl methacrylate.

The present invention comprises, in certain embodiments, a pharmaceutical composition suitable for oral administration to a human, comprising an active ingredient consisting essentially of an active ingredient according to a compound as described above.

DETAILED DESCRIPTION OF THE PREFERRED EMBODIMENT

Definitions

Figures 1A, 1B, 1C, 1D:
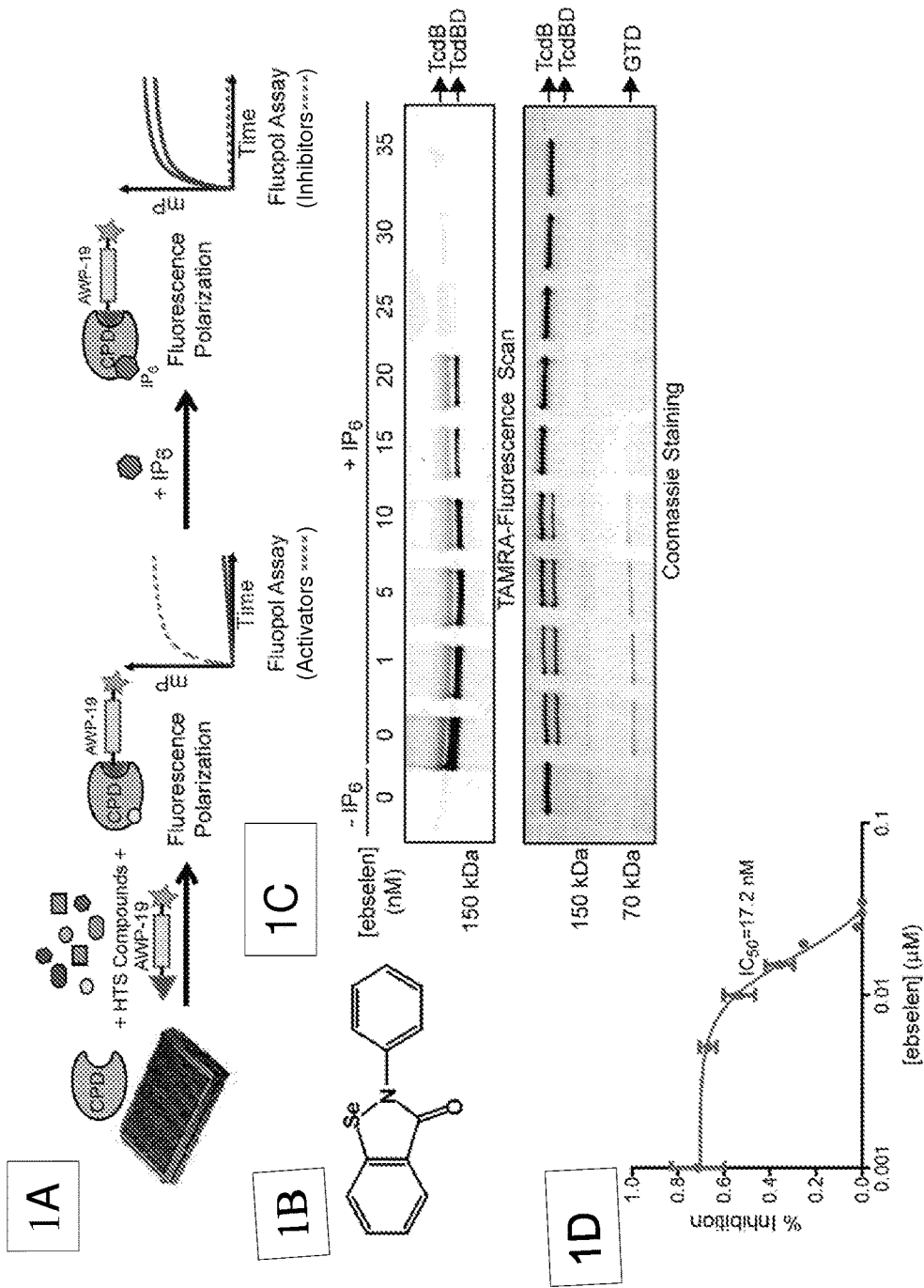
FIG. 1A, 1B, 1C, 1D is a schematic representation of the screen used to identify inhibitors of TcdB CPD activation, a chemical structure, fluorescence and staining images, and graph, respectively. Ebselen was found to inhibit TcdB activation and GTD cleavage.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

As used herein, the term "treat", "treating" or "treatment" of a clinical condition, such as a bacterial toxicity, associated with the physiological reaction to a toxin, includes: (1) preventing the clinical condition, i.e., causing the clinical condition not to develop in a mammal; (2) inhibiting the clinical condition, i.e., arresting or reducing the development of the clinical condition, or ameliorating the toxic symptoms or biological effect; or (3) relieving the clinical condition, i.e., causing regression of the clinical condition.

Unless otherwise specified, the term "substituted," as used herein, pertains to a parent group or compound which bears one or more substituent atoms. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

The term "alkyl," as used herein, pertains to a monovalent moiety obtained by removing a hydrogen atom from a carbon atom of a hydrocarbon compound having from 3 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkenyl, cylcoalkynyl, etc., discussed below.

The term "alkoxy," as used herein, pertains to an alkyl group attached to an oxygen (O-alkyl). Exemplary alkoxy groups include, but are not limited to, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, etc.

Hydrogen: —H. Note that if the substituent at a particular position is hydrogen, it may be convenient to refer to the compound or group as being "unsubstituted" at that position.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

Halo (or halogen): —F, —Cl, —Br, and —I.

Hydroxyl: —OH.

The term "toxicity" is used to the common medical definition and, as will be described, includes clinical symptoms such as watery diarrhea and cramps, as well as anatomical alterations in the affected tissue.

The term "ebselen", a known a mimic of glutathione peroxidase, 2-phenyl-1, 2-benzisoselenazol-3-one, has the following structure:

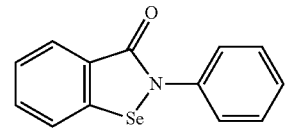 [SMILES: O=c1c2ccccc2[se]n1-c1ccccc1]

As the term is used herein, the compound ebselen in a composition includes salts and prodrugs as described below.

The term "*Clostridium difficile*," or *C. difficile*, is used in its conventional sense to refer to an obligate anaerobic, spore-producing, gram-positive rod that was first described in 1935. Its link with pseudomembranous colitis and *Clostridium difficile* infection (CDI) was established in 1978. The genes that encode toxins A, tcdA, and B, tcdB, are found on the pathogenicity locus in *C. difficile*. These genes are situated in close proximity on this locus and are transcribed in the same direction. Three other genes, tcdC, tcdD, and tcdE, are also located on the pathogenicity locus and are believed to play a role in regulation of toxin production. The tcdC gene lies downstream of tcdA and is transcribed in the opposite direction from tcdA and tcdB. It functions as a negative regulator of toxin production. The tcdD gene is found upstream from tcdB and is believed to be a major positive regulator of toxins A and B production. The tcdE gene lies between tcdA and tcdB and is believed to facilitate the release of toxins A and B through permeabilization of the *C. difficile* cell wall. TcdA and TcdB are further described at GenBank: CAA63564.1 and GenBank: CDF47237.1. It is understood that variants of these sequences exist. See, e.g., Lanis et al. "Variations in TcdB Activity and the Hypervirulence of Emerging Strains of *Clostridium difficile*," PLoS Pathog. 2010 August; 6(8): e1001061. Published online 2010 Aug. 19. doi:

The terms pharmaceutical composition and oral formulation are used in a conventional sense as referenced, e.g. in EP 1589951, mentioned below. The term "pharmaceutical composition" is intended to generally cover not only a single dosage form which is taken or administered at one single dose, such as tablet, capsule or injection, but also plural dosage forms which are administered at two or more divided doses. For example, the term "pharmaceutical composition containing ebselen or ebselen analogs include a pharmaceutically acceptable salt thereof, a solvate thereof or a hydrate thereof such compound, a solvate thereof or a hydrate thereof as protease inhibitor is interpreted to designate not only a single dosage form containing these two active ingredients all together, but also two dosage forms in which each contains one active ingredient. That is, where these two dosage forms are simultaneously administered or are consecutively administered at regular intervals and therefore effective amounts of two active ingredients contained in each of these dosage forms coexist in vivo to bring about synergistic effects, these two dosage forms also fall within the scope of the pharmaceutical composition containing ebselen or ebselen equivalent as described herein.

As oral formulation refers to a pharmaceutical formulation suitable for enteral or oral administration via: capsules, cachets, soft elastic gelatin capsules, hard gelatin capsules, tablets, caplets; as aerosols sprays; as a powder or granules; as a solution or a suspension in a non-aqueous liquid, an oil-in-water emulsion, or a water-in-oil liquid emulsion each containing a predetermined amount of the active ingredients. Since the present oral formulations are prepared for the treatment of *Clostridium* species, the oral formulation of the present compounds. For example, a tablet may be a compressed preparation that contains 5-10% of the active substance; 80% fillers, disintegrants, lubricants, glidants, and binders; and 10% of compounds which ensure easy disintegration, disaggregation, and dissolution of the tablet in the stomach or the intestine (colon). Thus a colon retentive formulation is an oral formulation that may be in a colon-specific delivery system as described below.

Overview

Described herein is the development and use of ebselen and ebselen-related compounds for use as a potent and safe in-human low nanomolar inhibitor of the cysteine protease domain of TcdB. Importantly, this drug is capable of effectively mediating histopathology of disease via oral administration showing for the first time that chemical inhibition of a primary virulence factor can block *C. difficile* pathogenesis of host tissues without using antibiotic pressure. Recent findings[25] demonstrating that toxin induced cell death is dependent on reactive oxygen species (ROS), raises the possibility that ebselen could confer protection both by direct toxin inactivation and through its ability to counteract ROS effects. Currently we are working on advancing efforts to repurpose this clinical drug candidate for the treatment of CDI either as a monotherapeutic or as a complement to first line antibiotics. We believe ebselen can significantly ameliorate not only the symptoms of initial onset CDI but also lower the recurrence rate and play a beneficial role in the restoration of the natural microbiota in patients.

The salt of the above-mentioned compound is not particularly limited as long as it is a pharmaceutically acceptable salt, and examples thereof include salts with an inorganic acid such as hydrochloric acid, nitric acid or sulfuric acid, salts with an organic acid such as acetic acid, fumaric acid, maleic acid, succinic acid or tartaric acid, and the like. The above-mentioned compound may be in the form of a solvate.

Oral preparations such as tablets, capsules, granules, fine granules and powders can be prepared using an extender such as lactose, crystalline cellulose, starch or vegetable oil, a lubricant such as magnesium stearate or talc, a binder such as hydroxypropyl cellulose or polyvinyl pyrrolidone, a disintegrant such as carboxymethyl cellulose calcium or low-substituted hydroxypropylmethyl cellulose, a coating agent such as hydroxypropylmethyl cellulose, macrogol or a silicone resin, a film forming agent such as gelatin film, and the like, as needed.

Colon-Specific Delivery Systems for Ebselen and Functional and Structural Analogues In certain aspects, the present invention comprises the preparation of ebselen or an ebselen analogue or *C. difficile* toxin inhibitor in a colon-specific pharmaceutical formulation (i.e. a colon-retentive or colon-releasing formulation). Targeting of drugs to the colon via oral administration protects the drug from degradation or release in the stomach and small intestine. It also ensures abrupt or controlled release of the drug in the proximal colon.

Examples of colon-specific pharmaceutical formulations are given in "Use of a mixture of two or more enteric materials to regulate drug release via membrane or matrix for systemic therapeutics, EP 1589951 A2 published Nov. 2, 2005. As described there, a "pharmaceutical composition", i.e. one containing the present ebselen or ebselen structural analogue, is prepared in combination with other materials that make it suitable for administration to a "patient" (human or other mammal) for therapeutic purposes by inhibition of CDI. The "core" contains the active ingredient(s) and is prepared by processes known in the art by combining the active ingredient(s) with other ingredients such as fillers, binders and other customary excipient ingredients, depending in part on the dosage form intended, and formed into tablets, beadlets, pellets and/or granules or other particles. It will be understood that when the term "ingredient" is used herein, it may refer to a singular-substance or two or more substances.

A coating containing two or more enteric materials surrounds the core. 'Enteric materials" are polymers that are substantially insoluble in the acidic environment of the stomach, but are predominantly soluble in intestinal fluids at specific pHs. The enteric materials are non-toxic, pharmaceutically acceptable polymers, and include, for example, cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit 5100, Kollicoat EMM30D, Estacryl 30D, Coateric, and Aquateric). The foregoing is a list of possible materials, but one of skill in the art would recognize that it is not comprehensive and that there are other enteric materials that would meet the objectives of the present invention of providing for a sustained/accelerated release profile. The coating contains two or more enteric polymers that are soluble at different pHs. These solubilities are either known or readily determinable in vitro. Hydroxypropyl methylcellulose phthalate (HPMCP), polyvinyl acetate phthalate (PVAP) and Coateric will dissolve in buffers of pH 5.0 and higher. Eudragit L100-55, Eudragit L30D-55, Kollicoat EMM30D, and Estacryl 30D will dissolve from pH5.5 to 6.5. Cellulose acetate phthalate (CAP) and Aquateric will dissolve in buffers above pH 6.2. Eudragit S100 and FS30D will dissolve around pH7.0-7.5. Roughly, the pH of the duodenum is about 5.5, the jejunum is about 6.5 and the distal ileum is about 7.5.

The formulation used in the present invention is designed to target the presumed location of the *C. difficile* infection and/or its released toxins. *C. difficile* is usually found in the colon membranes. Abdominal computed tomography (CT) scanning is the imaging modality of choice for *C. difficile* colitis when pseudomembranous colitis, other complications of CDI, or other intra-abdominal pathology is suspected. In patients with sepsis due to suspected megacolon, abdominal radiography may be performed instead of CT scanning to establish the presence of megacolon in a timely manner. Endoscopy is less sensitive for diagnosing *C. difficile* than are stool assays. Endoscopy may demonstrate the presence of raised, yellowish-white, 2- to 10-mm plaques overlying an erythematous and edematous mucosa. These plaques are termed pseudomembranes. Endoscopic examination findings may be normal in patients with mild disease or may demonstrate nonspecific colitis in moderate cases.

In some cases the present ebselen compounds may be prepared as prodrugs that are converted into active compounds in the colon, Chourasia M K et al "Pharmaceutical approaches to colon targeted drug delivery systems," J Pharm Sci. 2003 January-April; 6(1):33-66 may be consulted for further details. Briefly, as described there, various strategies for targeting orally administered drugs to the colon include covalent linkage of a drug with a carrier, coating with pH-sensitive polymers, formulation of timed release systems, exploitation of carriers that are degraded specifically by colonic bacteria, bioadhesive systems and osmotic controlled drug delivery systems. Various prodrugs (sulfasalazine, ipsalazine, balsalazine and olsalazine) have been developed that are aimed to deliver (for example, 5-amino salicylic acid (5-ASA) for localized chemotherapy of inflammatory bowel disease (IBD)). Microbially degradable polymers, especially azo crosslinked polymers, have been investigated for use in targeting of drugs to colon. Certain plant polysaccharides such as amylose, inulin, pectin and guar gum remains unaffected in the presence of intestinal enzymes and pave the way for the formulation of colon targeted drug delivery systems. In one formulation, 2-phenyl-1,2-benzoselenazol-3-one or analogs will be entrapped into chitosan cores and Eudragit S100/Eudragit L100. Redox sensitive polymers and bioadhesive systems may also be exploited to deliver the drugs into the colon.

Exemplary Patient Population

In certain aspects, the present invention comprises determining the existence of a CDI infection prior to administration of the present compositions. Monitoring the infection during a course of treatment is also contemplated.

The presentation of *C. difficile* infection can range in severity. Symptoms can range from mild to fulminant and may include diarrhea, fever, cramping, abdominal discomfort and distension, colonic ileus, toxic dilatation, and sometimes fatal pseudomembranous colitis. *C. difficile* should be suspected in any patient with diarrhea who has taken antibiotics during the previous 3 months, or when diarrhea develops during or soon after hospitalization. Criteria for the diagnosis of CDI are taken from the SHEA/IDSA guidelines, published in 2010. The diagnosis of CDI should be based on a combination of clinical and laboratory findings. A case definition for the usual presentation of CDI includes the following findings:

1. The presence of diarrhea, defined as passage of 3 or more unformed bowel movements (UBMs) in 24 or fewer consecutive hours.
2. A positive stool test result for the presence of toxigenic *C. difficile* or its toxins, or colonoscopic or histopathologic findings demonstrating pseudomembranous colitis.

The same criteria should be used to diagnose recurrent CDI. Toxin enzyme immunoassay (EIA), which detects *C. difficile* toxins A and B, may also be used due to its speed, specificity, and convenience, but it may lack sensitivity.

General Method and Materials

Protein Expression and Purification.

CPD domain was expressed and purified according to Shen et al[23]. The full length toxin B (TcdB) expression vector was a gift from Dr. Dana Borden Lacy. The expression of this construct was performed according to Yang et al[34].

High Throughput Screen Analysis.

Fluorescence polarization high throughput screen was performed and analysis carried out at the Stanford High Throughput Bioscience Center (HTBC, htbc.stanford.edu).

Inhibition of TcdB AWP-19 Probe Labeling Assay. Full length TcdB was diluted into CPD buffer [60 mM NaCl, 20 mM Tris pH 8] to a final concentration of 100 nM, following the incubation with ebselen for 1 hr at 37° C. in a volume of 15 µL. AWP-19 was added to a final concentration of 2 µM (1:20 dilution of a DMSO stock). $IP_6$ (Sigma) was added (1:20 dilution from stock in water) to the 70 µM final concentration. AWP-19 labeling was allowed to proceed for 20 minutes at 37° C. after which 4×SDS sample buffer was added. The reaction was boiled for 3 minutes at 95° C. and the samples were resolved by SDS-PAGE (4-20% gradient gel, Biorad). The gel was scanned using a Typhoon imager and then Coomassie stained to ensure equal loading. Experiments were performed in triplicate.

$IC_{50}$ Determination. Labeling reactions were quantified in triplicate using the program ImageJ (imagej.nih.gov(slash) ij, National Institutes of Health). The absolute value for each ebselen concentration was averaged and then corrected by subtracting the average value at 0 µM ebselen with $IP_6$. The corrected values were plotted against ebselen concentration, and the $IC_{50}$ (the concentration of inhibitor that produced half-maximal labeling) was determined using the non-linear regression fitting using GraphPad Prism.

Cell Rounding Assay. Human foreskin fibroblast, cultured in Dulbecco's modified medium (DMEM), supplemented with 10% (v/v) fetal calf serum, 100 µg/ml penicillin, and 100 mM streptomycin, were plated in 24 well dishes and grown to confluency. Volume of DMEM was 1 mL. Cells were treated with TcdB (100 pM final concentration) pre-treated with DMSO or increasing amounts of ebselen from 20× stock solutions for 60 minutes in 15 µL CPD buffer. Control cells were treated with reaction vehicle (CPD buffer with 0.75 µL DMSO) and were left untreated or were treated with the same amount of toxin. For the ebselen-pretreated assay, cells were treated with increasing amounts of ebselen (1 µL in DMSO), washed 3 times in DMEM and challenged with TcdB (100 pM final concentration) for 60 minutes. Control cells were pre-treated with 1 µL DMSO and left untreated or challenged with the same amount of toxin. Round cells were counted using a Leica microscope eye-piece counting grid and results expressed as percentage of total cells. Assay for cell rounding induced by feces samples from mice infected with *C. difficile* strain 630 was performed as follows: feces were resuspended in 4× (w/v) PBS and homogenized using a micropellet homogenizer. Samples were centrifuged for 15 minutes at 5000 g and feces supernatant filtered through a sterile 0.45 micron membrane filter. Samples were diluted at indicated concentrations with PBS and applied to the cells at the final volume of 2 µL. Cell rounding was determined as described above. $EC_{50}$ values were determined using GraphPad Prism.

Bacterial Strains and Culture Conditions. *C. difficile* strain 630 was used in a mouse model of disease in all *C. difficile* experiments and was cultured in Brain Heart Infusion (Becton Dickinson, MD) supplemented with 5 mg/ml of Yeast Extract (Remel) (BHIS) anaerobically (6% $H_2$, 20% $CO_2$, 74% $N_2$)[3]. For quantification of *C. difficile* CFU in conventional mice, 1 µl of feces was serially diluted in PBS and plated onto CDMN plates, composed of *C. difficile* agar base (Oxoid) with 7% v/v of defibrinated horse blood (Lampire Biological Laboratories), supplemented with 32 mg/µl moxalactam (Santa Cruz Biotechnology) and 12 mg/µl norfloxacin (Sigma-Aldrich). Plates were incubated overnight at 37° C. in an anaerobic chamber (Coy).

Mouse Toxigenic Model. Mouse TcdB toxigenic experiments were performed according to A-PLAC, Stanford IACUC. The toxigenic model was adapted from Lanis et al[35]. Full length toxin was sterilely filtered using Corning CostarSpin-X Centrifugal Filter Devices (with 0.22 μm pore diameter) to ensure that the injection itself was not painful to the animal and did not cause abscesses. Two groups of mice, ebselen- and control-treated, were i.p. injected with TcdB (1 μg toxin/kg mice final, in a volume of 100 μL) pretreated with 100 nM ebselen or DMSO for 1 hr.) Mice were monitored for toxicity symptoms and scored using the following clinical score: 0=healthy animal, 1=ruffled fur and BAR (bright, alert, and reactive), 2=ruffled fur, hunched and QAR (quiet, alert, and reactive), 3=ruffled fur, hunched, inactive, dehydration, 4=moribund (rapid breathing, hemiparesis, tachypneic state, grimacing, hypothermia, peritoneal swelling, hunched inactive, dehydration). Mice scored at 4 were sacrificed according to the A-PLAC protocol and considered as being in the "mortality" endpoint population in the study. Fraction survival plots were created using death as the time point when moribund animals were scored at clinical score 4 (time of sacrifice) using GraphPad Prism.

Mouse C. difficile Infection Model. Conventional Swiss-Webster mice (RFSW, Taconic) were maintained in accordance with A-PLAC, the Stanford IACUC. Prior C. difficile challenge antibiotics were administered in the drinking water for 3 days, starting 6 days before inoculation including: kanamycin (0.4 mg ml$^{-1}$), gentamycin (0.035 mg ml$^{-1}$), colistin (850 U ml$^{-1}$), metronidazole (0.215 mg ml$^{-1}$) and vancomycin (0.045 mg ml$^{-1}$)[3]. Mice were switched to regular water for 2 days, followed by the administration of 1 mg of clindamycin administered via oral gavage 1 day before C. difficile inoculation with $10^8$ CFU from overnight cultures via oral gavage. Mouse feces used for CFU counts and cell rounding assays were collected daily prior to oral gavages with ebselen.

Ebselen Treatment. 15 mice were used for each experiment (8 ebselen-treated and 7 vehicle-treated). Mice were treated with ebselen starting with the first dose 2 hours prior to C. difficile challenge, followed by daily gavages with ebselen at 2 pm for 4 days. The daily dose of ebselen was 100 mg/kg in 200 μL final volume. The compound was dissolved in DMSO, and then resuspended in a 1:4 DMSO-oil microemulsion (v/v). The control group was treated with the vehicle only. Mice were sacrificed according to the guidelines on humane termination on day 5 after the infection and their colons were submitted for preparation for histological analysis.

Histochemistry and Histopathological Scoring. Proximal colon and cecum sections were collected and fixed in 10% formalin for 24 hours, then stored in 70% ethanol. Cassettes were paraffin embedded, sectioned, mounted on slides and stained with the hematoxylin-eosin stain (Histo-tec Laboratory, Hayward, Calif.). Histological specimens were scored by a blinded veterinarian pathologist (Dr. Richard Leung, Stanford VSC). The scoring system was adopted from Pawlovski et al[33]. The scale was 0-3 (minimal score, 0; maximal score, 3) and included the following pathological features: inflammatory cell infiltration, mucosal hypertrophy, vascular congestion, epithelial disruption, and submucosal edema.

Statistical Analyses. Histopathological, biochemical, and in vitro data were analyzed using GraphPad Prism 6 (GraphPad Software Inc., San Diego, Calif.), and expressed as mean±SEM. Statistical analyses were performed with the student t test unless stated differently. P values equal to or smaller than 0.05 were considered significant.

EXAMPLES

Example 1A

High Throughput Screen for Inhibitors of TcdB CPD

We have developed a fluorescence polarization high throughput screen (HTS) to identify inhibitors of the TcdB CPD (FIG. 1A). This screen makes use of a fluorescent small molecule activity based probe that covalently binds to the active site cysteine residue of the CPD to measure enzyme activity[2,23]. The unbound fluorescent activity based probe (AWP-19) produces low fluorescence polarization (mP). Probe binding to $IP_6$-activated CPD results in an increase in mP and the difference in bound and unbound mP values can be measured on a plate reader. Thus, the probe allows screening for both inhibitors and activators in an HTS format. Using this approach, we screened a large library of bioavailable drugs considered clinically safe but without an FDA approved use[28] as well as the National Institutes of Health Clinical Collection. The compounds were screened against the recombinantly expressed cysteine protease domain. The screen identified a number of inhibitors from both sets of compounds, shown in Table 1 below.

TABLE 1

Selected TcdB inhibitors from the Diversity compounds part of the screen (functional analogues)

| Structure | IC50 (μM) | STF number | R |
|---|---|---|---|
| (structure shown) | 3.992 | 102645 | 1-methyl-3-phenylpropylamine |

TABLE 1-continued

Selected TcdB inhibitors from the Diversity compounds part of the screen (functional analogues)

| Structure | IC50 (μM) | STF number | R |
|---|---|---|---|
| (structure) | 4.844 | 102635 | Methyl piperazine-1-carboxylate |
| (structure) | 1.315 | 102625 | 3-(cyclohexylsulfanyl)propylamine |
| (structure) | 3.144 | 102655 | 2-(4-chlorophenyl)ethylamine |
| (structure) | 1.977 | 102686 | butylamine |
| (structure) | 2.805 | 102644 | 3-ethoxypropylamine |
| (structure) | 2.385 | 102766 | 2-methoxyethylamine |
| (structure) | 3.903 | 102654 | 1,3-benzodioxol-5-ylmethylamine |

Exemplary compounds from the above table are:

Formula I

[Chemical structure: 4,6-dimethyl-isothiazolo[5,4-b]pyridin-3(2H)-one with N-CH2-C(O)-R substituent]

R in Formula I may be a radical such as shown above in Table 1. R may be, for example, an aryl alkylamine, piperazine substituted with carboxylate ester, cycloalkylsulfanyl alkylamine, aryl alkylamine with a halogen-substituted aryl, alkylamine, alkoxy alkylamine, or benzodioxolyl alkylamine.

Ebselen

Of particular interest was a highly potent inhibitor of toxin activation, ebselen (2-phenyl-1,2-benzoselenazol-3-one; FIG. 1B), currently in phase II clinical trials for the treatment of chemotherapy induced hearing loss and tinnitus. Furthermore, a previous phase III clinical trial demonstrated that ebselen improved the outcome of acute ischemic stroke[29]. Ebselen is a synthetic, low molecular weight seleno-organic compound effective in reducing a variety of oxidative stress mediated pathologies in animal models and is a modifier of a handful of bacterial virulence factors in vitro[30, 31]. It possesses glutathione peroxidase-like activity and reacts rapidly with peroxynitrite, a highly potent species that damages vital biomolecules. We chose to focus on this lead as it has proven to have low toxicity in humans and could allow direct validation of the CPD as a therapeutic target for CDI.

Compound Testing

Figures 2A, 2B, 2C, 2D:
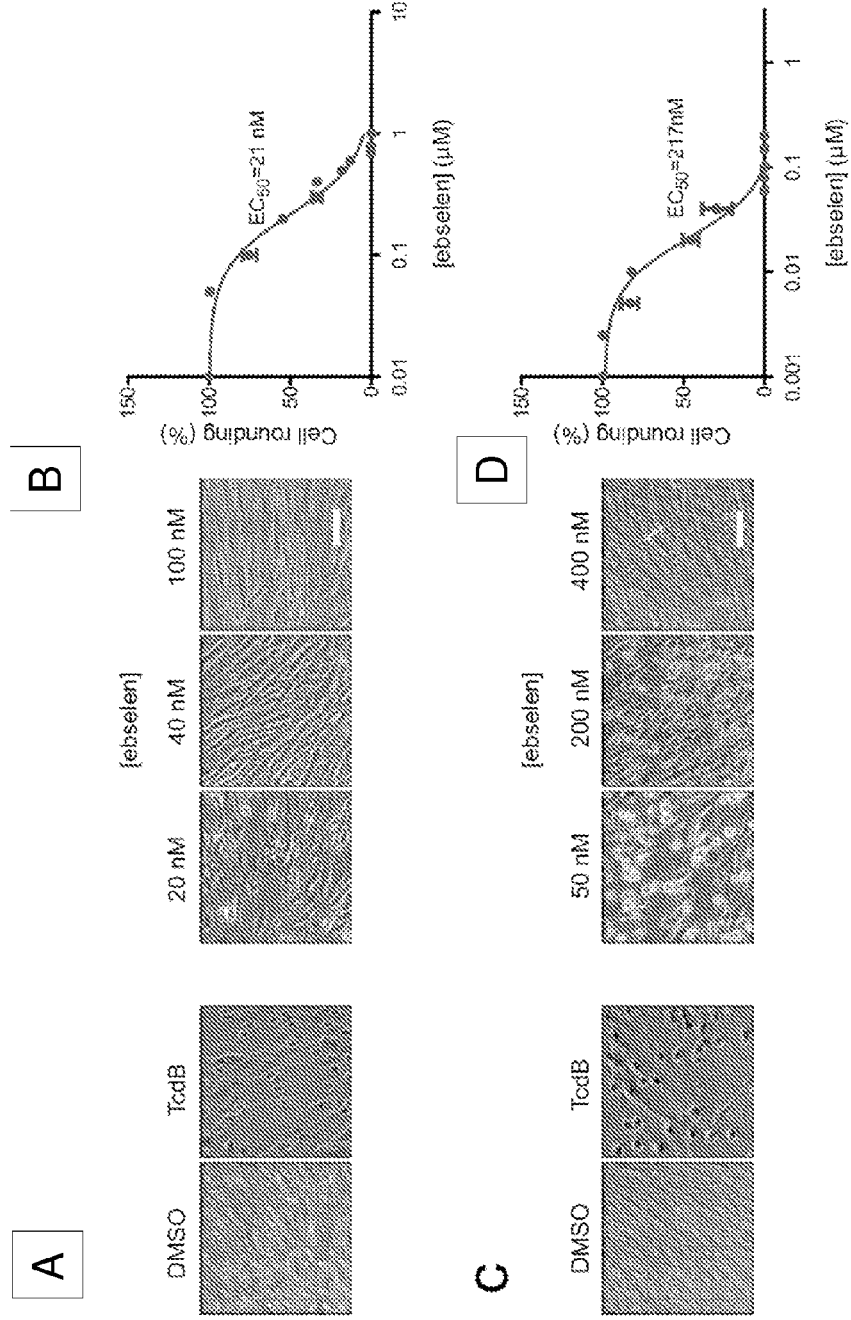
FIG. 2A, 2B, 2C, 2D consists of micrographs and line graphs showing that ebselen protects cells against TcdB induced toxicity.
Figure 5:
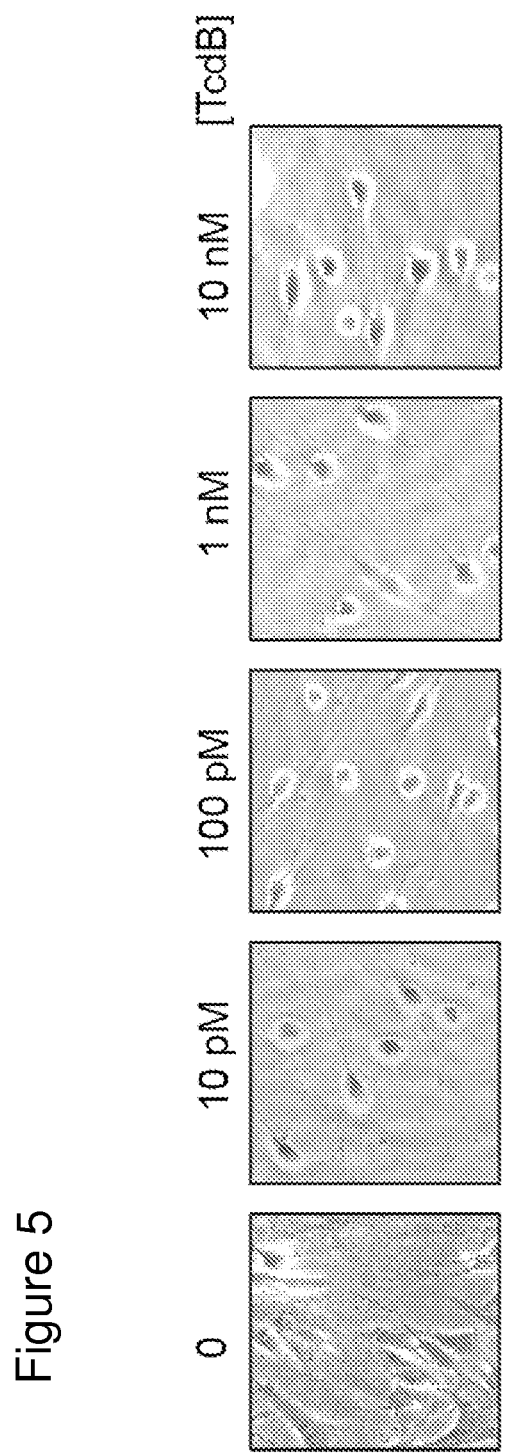
FIG. 5 is a series of photomicrographs showing HFF TcdB-induced cell rounding. Cells were treated with increasing amounts of TcdB ranging from 10 pM-10 nM final for 60 minutes and observed for cell rounding.

Detailed dose response profiling studies of ebselen against the native, full length toxin were conducted using a competition labeling assay with the active site probe (FIG. 1C). TcdB was incubated with increasing amounts of ebselen, activated with $IP_6$, and labeled with AWP-19. Samples were resolved by SDS PAGE and scanned for fluorescence or stained by Coomassie. Full length TcdB, TcdB that has proteolytically released the GTD ($TcdB_A$) as well as the GTD are indicated by arrows. Image shows a typical representation of three replicates. Ebselen completely inhibited the $IP_6$ induced release of the GTD domain at low nanomolar concentrations and inhibited labeling of the CPD with an $IC_{50}$ of 17.2 nM (FIG. 1D). Relative fluorescence units were normalized to RFU at 0+$IP_6$ and plotted as fraction of 0+$IP_6$ labeling intensity at increasing concentrations. Results are mean±SEM. To determine the activity of ebselen in vitro, we conducted a TcdB induced cell rounding assay in which the full length toxin was added to intact human fibroblasts and found that it induced potent cell protection, specifically, when a toxin concentration sufficient to induce 100% cell rounding in 60 minutes (FIG. 5) was pre-incubated with increasing concentrations of ebselen and applied to a monolayer of human fibroblasts (FIG. 2A). HFF cells were challenged with DMSO, DMSO treated-TcdB, or TcdB treated with the increasing amounts of ebselen. Images in FIG. 2A are representative for each sample type. Ebselen blocked cell rounding with an $EC_{50}$ of 21 nM (FIG. 2B). $EC_{50}$ values for cell rounding were calculated by counting of rounded cells and plotting as a percentage relative to the DMSO control using GraphPad Prism. Results are the mean of 3 biological replicates ±SEM. In addition, when HFF cells were pre-incubated with increasing concentrations of ebselen, washed, and then challenged with toxin (FIG. 2C), a complete protective effect was observed at sub-micromolar concentrations of the drug ($EC_{50}$ of 217 nM; FIG. 2D). $EC_{50}$ was calculated as in FIG. 2B. The results are representative of three biological replicates and the bars indicate 10 μm.

Example 1B

Ebselen Analogs Having TcdB Protease Inhibition

The data are for a competition based assay with an active site probe; it can be seen that some compounds in Table 2 are actually more potent than ebselen.

TABLE 2

| No. | IC50 (uM) | Structure/MF/MW | Name and rank: 1 = most inhibition (annotated inhibitors only) |
|---|---|---|---|
| MG-33 | 2.704 | [Structure of bis(2,4-difluorophenyl)benzamide diselenide] $C_{26}H_{16}F_4N_2O_2Se_2$ = 622.3310528 | 2,2'-diselane-1,2-diylbis[N-(2,4-difluorophenyl)benzamide]; 1 |

TABLE 2-continued

| No. | IC50 (uM) | Structure/MF/MW | Name and rank: 1 = most inhibition (annotated inhibitors only) |
|---|---|---|---|
| MG-56 | 3.946 | $C_{28}H_{14}N_2O_4Se_2 = 610.42116$ | 2,2'-diselane-1,2-diylbis[N-(3-methoxyphenyl)benzamide]; 2 |
| MG-12 | 3.976 | $C_{28}H_{22}Cl_2N_2O_2Se_2 = 647.31248$ | 2,2'-diselane-1,2-diylbis[N-(2-chloro-4-methylphenyl)benzamide]; 3 |
| MG-38 | 4.743 | $C_{26}H_{16}Cl_2F_2N_2O_2Se_2 = 655.2402464$ | 2,2'-diselane-1,2-diylbis[N-(2-chloro-4-methylphenyl)benzamide]; 3 |
| MG-174 | 4.864 | $C_{13}H_9NO_2Se = 290.17606$ | 2-(2-hydroxyphenyl)-1,2-benzoselenazol-3-one; 5 |
| MG-13 | 4.897 | $C_{14}H_{11}NOSe = 288.20324$ | 2-(4-methylphenyl)-1,2-benzoselenazol-3-one; 6 |

TABLE 2-continued

| No. | IC50 (uM) | Structure/MF/MW | Name and rank: 1 = most inhibition (annotated inhibitors only) |
|---|---|---|---|
| MG-31 | 4.917 | 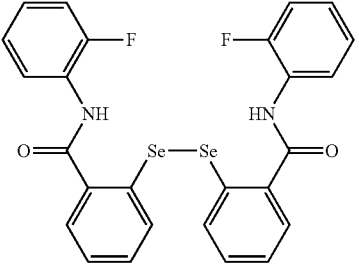 $C_{26}H_{18}F_2N_2O_2Se_2$ = 586.3501264 | 2,2'-diselane-1,2-diylbis[N-(2-fluorophenyl)benzamide]; 7 |
| MG-43 | 5.092 | 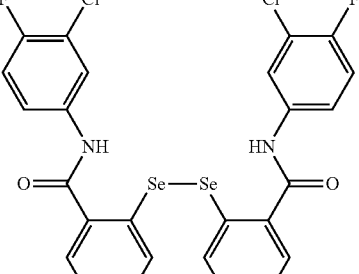 $C_{26}H_{16}Cl_2F_2N_2O_2Se_2$ = 655.2402464 | 2,2'-diselane-1,2-diylbis[N-(3-chloro-4-fluorophenyl)benzamide]; 8 |
| EBSELEN | 5.136 | 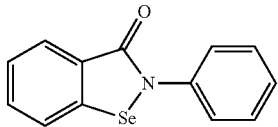 $C_{13}H_9NOSe$ = 274.17666 | 2-phenyl-1,2-benzoselenazol-3-one; 9 |
| MG-2 | 5.577 | 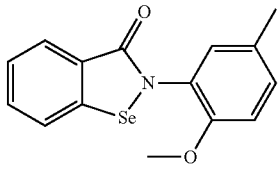 $C_{15}H_{13}NO_2Se$ = 318.22922 | 2-(2-methoxy-5-methylphenyl)-1,2-benzoselenazol-3-one; 10 |
| MG-61 | 5.973 | 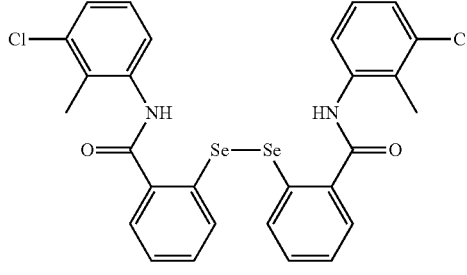 $C_{28}H_{22}Cl_2N_2O_2Se_2$ = 647.31248 | 2,2'-diselane-1,2-diylbis[N-(3-chloro-2-methylphenyl)benzamide]; 11 |

TABLE 2-continued

| No. | IC50 (uM) | Structure/MF/MW | Name and rank: 1 = most inhibition (annotated inhibitors only) |
|---|---|---|---|
| MG-1 | 6.471 | 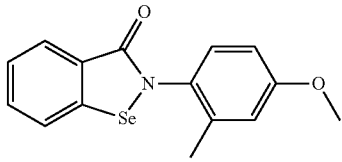<br>C₁₅H₁₃NO₂Se = 318.22922 | 2-(4-methoxy-2-methylphenyl)-1,2-benzoselenazol-3-one; 12 |
| MG-34 | 6.5 | 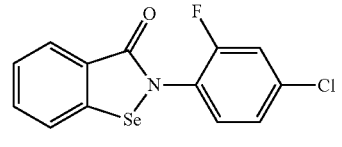<br>C₁₃H₇ClFNOSe = 326.6121832 | 2-(4-chloro-2-fluorophenyl)-1,2-benzoselenazol-3-one; 13 |
| MG-10 | 7.334 | 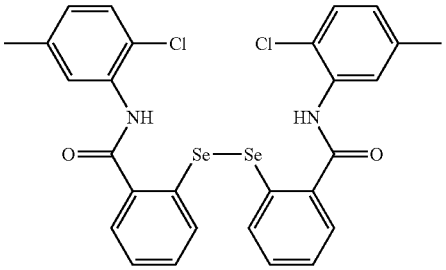<br>C₂₈H₂₂Cl₂N₂O₂Se₂ = 647.31248 | 2,2'-diselane-1,2-diylbis[N-(2-chloro-5-methylphenyl)benzamide]; 14 |
| MG-40 | 7.384 | 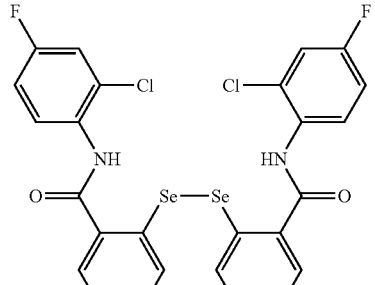<br>C₂₆H₁₆Cl₂F₂N₂O₂Se₂ = 655.2402464 | 2,2'-diselane-1,2-diylbis[N-(2-chloro-4-fluorophenyl)benzamide]; 15 |
| MG-48 | 7.44 | 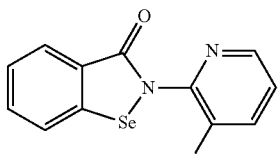<br>C₁₂H₈N₂O₂Se = 291.16412 | 2-(3-hydroxypyridin-2-yl)-1,2-benzoselenazol-3-one; 16 |
| MG-8 | 8.501 | 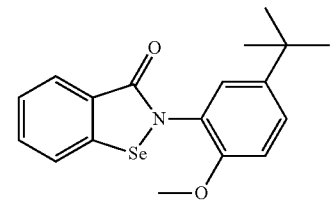<br>C₁₈H₁₉NO₂Se = 360.30896 | 2-(2-methoxy-5-t-butylphenyl)-1,2-benzoselenazol-3-one; 17 |

TABLE 2-continued

| No. | IC50 (uM) | Structure/MF/MW | Name and rank: 1 = most inhibition (annotated inhibitors only) |
|---|---|---|---|
| MG-7 | 9.6 | 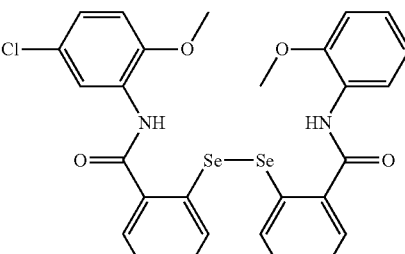 $C_{28}H_{22}Cl_2N_2O_4Se_2 = 679.31128$ | 2,2'-diselane-1,2-diylbis[N-(5-chloro-2-methoxyphenyl)benzamide]; 18 |

Table 2 contains 17 compounds synthesized and tested according to the present invention. Compound No. 9 is ebselen. Compounds 1-8 had a measured IC50 (μM) of less than ebselen. The compounds may be described by Formula II and Formula III:

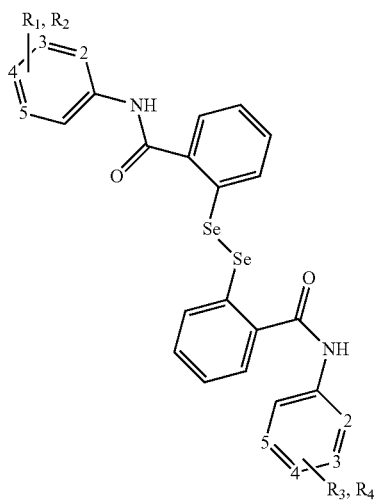

Formula II

The above shown Formula II represents a variety of substituents, $R_1$ and $R_2$ in one phenyl group, and $R_3$ and $R_4$ in a second phenyl group. Substituents $R_1$-$R_4$ are indicated in Table I, in which the numeric prefixes identify the ring carbon, as numbered in Formula II, to which the substituent binds. As shown, $R_1$-$R_4$ may comprise:

| Compound | $R_1$ | $R_2$ | $R_3$ | $R_4$ |
|---|---|---|---|---|
| MG-33 | 2: F | 4: F | 2: F | 4: F |
| MG-56 | 3: OCH$_3$ | H | 3: OCH$_3$ | H |
| MG-12 | 2: Cl | 4: CH$_3$ | 2: Cl | 4: CH$_3$ |
| MG-38 | 2: Cl | 6: F | 2: Cl | 6: F |
| MG-31 | 2: F | H | 2: F | H |
| MG-43 | 3: Cl | 4: F | 3: Cl | 4: F |
| MG-61 | 3: Cl | 2: CH$_3$ | 3: Cl | 2: CH$_3$ |
| MG-10 | 2: Cl | 5: CH$_3$ | 2: Cl | 5: CH$_3$ |
| MG-40 | 2: Cl | 4: F | 2: Cl | 4: F |
| MG-7 | 5: Cl | 2: OCH$_3$ | 5: Cl | 2: OCH$_3$ |

Formula III is shown below:

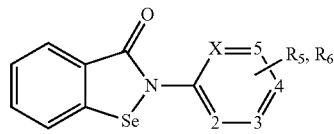

$R_5$, $R_6$ and X are illustrated as follows, with the numeric prefixes for $R_5$ and $R_6$ identifying the ring carbon, as numbered in Formula III, to which the substituent binds:

| compound | $R_5$ | $R_6$ | X |
|---|---|---|---|
| MG-174 | 2: OH | H | C |
| MG-13 | 4: CH$_3$ | H | C |
| MG-2 | 2: OCH$_3$ | 5: CH$_3$ | C |
| MG-1 | 4: OCH$_3$ | 2: CH$_3$ | C |
| MG-34 | 4: Cl | 2: F | C |
| MG-48 | 2: OH | H | N |
| MG-8 | 2: OCH$_3$ | 5: t-butyl | C |

Example 2

In Vivo Efficacy of Ebselen Against TcdB

Figures 3A, 3B:
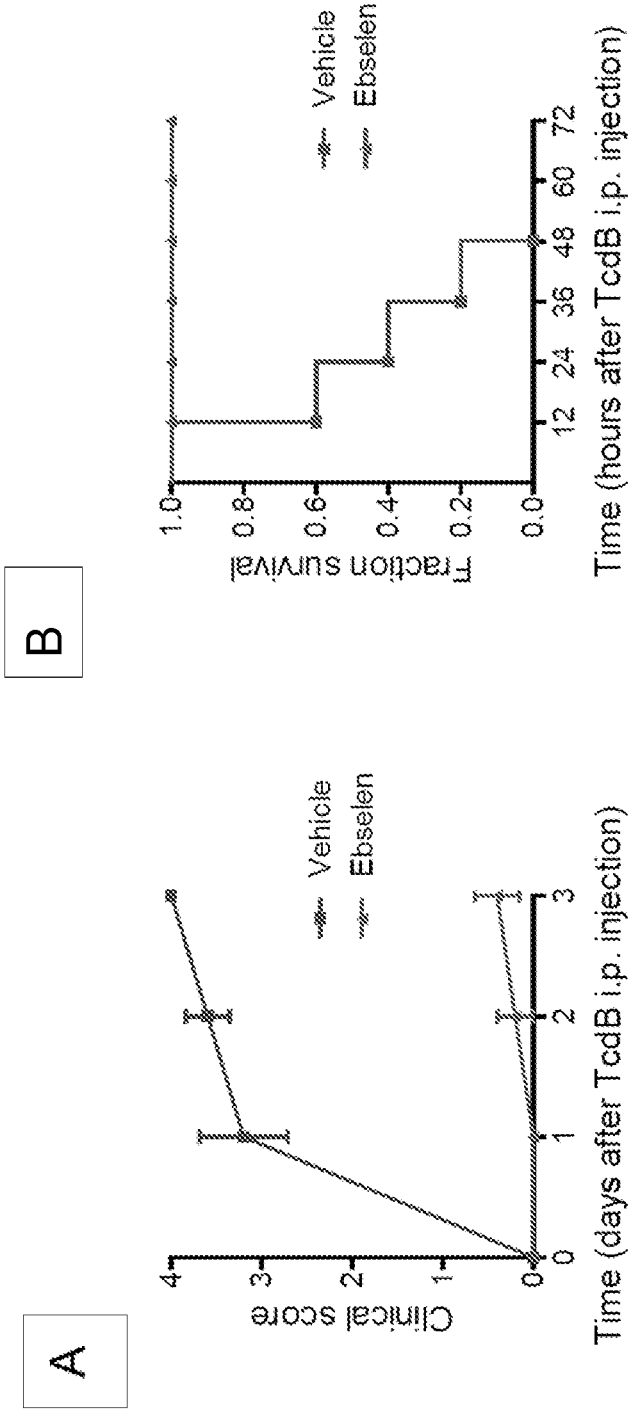
FIG. 3A, 3B gives a line graph and survival plot showing that ebselen protects mice from toxic effects of TcdB.

To determine the efficacy of ebselen against the toxin in vivo, two groups of mice (5 mice per group) were injected intra peritoneally (i.p.) with either 25 ng TcdB or with 25 ng TcdB that had been pretreated with 100 nM ebselen. Mice were monitored for three days for clinical signs of toxin action and overall survival. Mice treated with the ebselen-pretreated TcdB had a 100% survival rate with no significant changes in vital signs (FIG. 3A) while the control group showed significant signs of toxicity (ruffled fur, significantly decreased activity, peritoneal swelling, and hunched position) by 12 hours after toxin injection. Clinical scoring throughout 72 hours was assessed as follows: 0=healthy animal, 1=ruffled fur and BAR (bright, alert, and reactive), 2=ruffled fur, hunched and QAR (quiet, alert, and reactive), 3=ruffled fur, hunched, inactive, dehydration, 4=moribund. Overall, the untreated group had a 60% mortality rate within the first 24 hours and a 100% mortality rate by the end of day 3 (FIG. 3B). Survival plots were compiled with GraphPad Prism using the Kaplan Meier Method using animals scored at 4 (moribund) as the endpoint prior humane termination. The Chi-squared statistic was 10.90 with an associated P-value of less than 0.001. Thus, inhibition of the CPD by ebselen efficiently blocked the function of the toxin in vivo, resulting in complete protection from toxin systemic lethality.

Example 3

In Vivo Efficacy of Ebselen in a Mouse Model of CDI

Figures 4A, 4B, 4C, 4D, 4E:
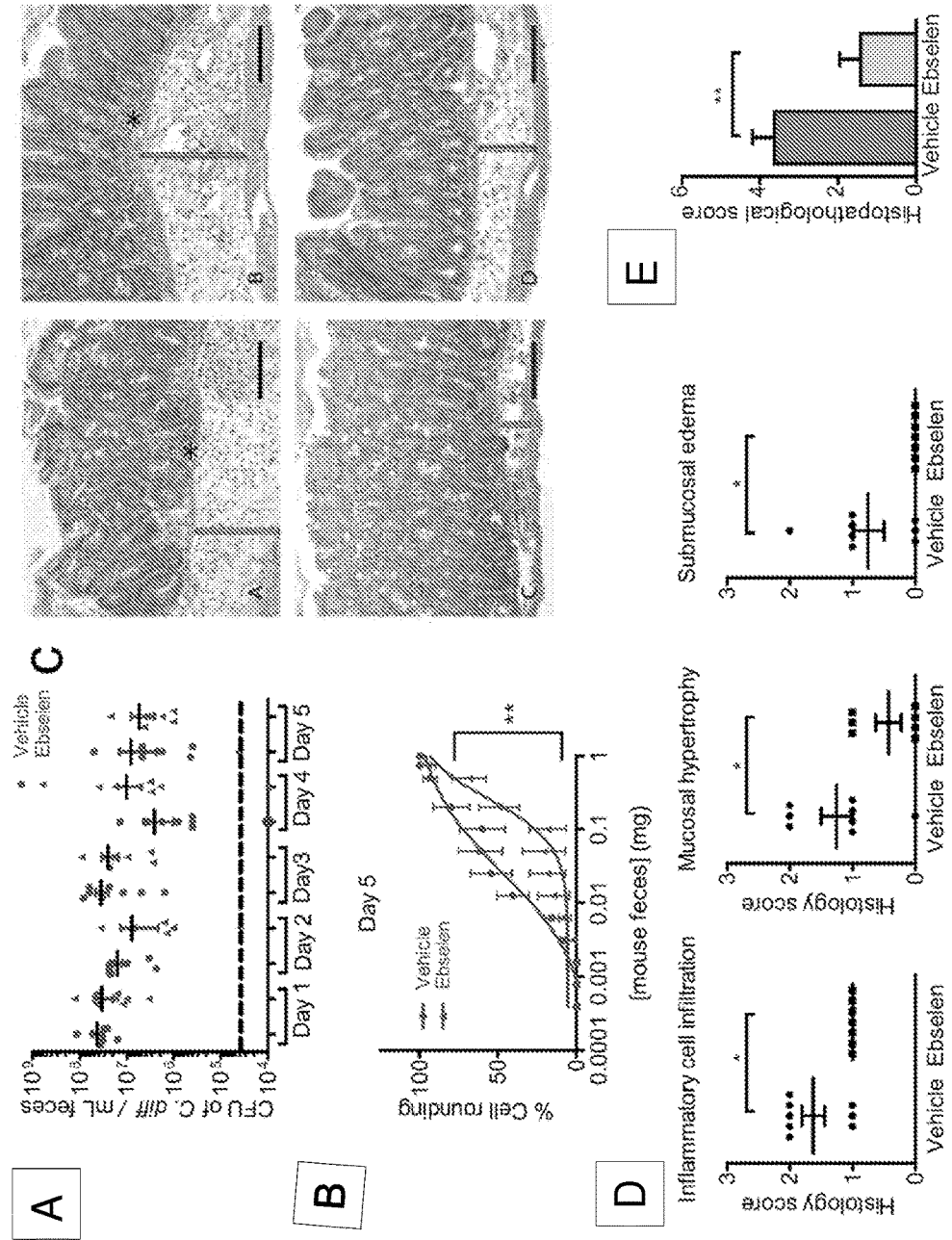
FIG. 4A, 4B, 4C, 4D, 4E gives data plots, graphs and photomicrographs showing that ebselen treatment reduces amount of active toxin from C. difficile 630 strain infected mice and significantly blocks the histopathology upon C. difficile infection.

As a final and most clinically relevant test of the potential value of ebselen for treatment of CDI, we performed a drug trial in a mouse model that closely mimics the human disease[3]. To generate this model, mice were exposed to a mixture of antibiotics (kanamycin, gentamicin, colistin, metronidazole, and vancomycin) for 3 days to eliminate the natural gut microbiota. Two days later, the mice were treated with clindamycin and then 24 hours later challenged with *C. difficile* strain 630, a virulent and multi-drug resistant strain of epidemic type X[32]. In this model, mice develop CDI with a peak in symptoms such as weight loss, hunched position, wet tail and diarrhea at days 2 and 3 post-infection. Immediately following infection, mice were treated with 100 mg/kg ebselen or vehicle daily via oral gavage for up to 5 days. Throughout the trial, fecal pellets were collected and used to determine the *C. difficile* bacterial burden count and to measure levels of TcdB-induced cell rounding. As expected, comparing *C. difficile* colony forming unit (CFU) counts from fecal samples for ebselen- and vehicle-treated mice, we did not observe a significant difference between the two groups throughout the five day experiment (FIG. 4A). However, we did see a significant reduction in the shed-toxin induced $EC_{50}$ of cell-rounding ($EC_{50}$ equals mg of feces required for 50% cell rounding; FIG. 4B) suggesting that the drug was able to block toxin function. The dose response plots in FIG. 4B show the activity of TcdB toxin in feces of vehicle- and ebselen-treated mice at day 5 post *C. difficile* infection. The indicated µg of feces equivalents collected from *C. difficile*-infected mice treated with ebselen (triangles, n=8) or vehicle (circles, n=7) were resuspended in PBS and applied to HFF cells. Cell rounding was calculated as the percentage of rounded cells relative to DMSO control treated cells, and results are given as mean±SEM. Samples were statistically analyzed using paired t test, with ** indicating P<0.01. This data confirms that the drug was orally bioavailable and able to inhibit the intended target in vivo.

Example 4

Histopathological Analysis of Tissues of Infected and Treated Mice

Finally to assess the overall effects of ebselen on tissue pathogenesis, we analyzed sections from the cecum and proximal colon of infected and treated mice by histopathological analysis at day 5 post-infection (FIG. 4C). An independent pathologist, blinded to the clinical data, scored the samples. Samples were analyzed for inflammatory cell infiltration, submucosal edema and mucosal hypertrophy, as well as for the vascular congestion and epithelial disruption[33]. The images of colon tissues from mice infected with *C. difficile* show that in the control animals (4A, 4B), there is moderate neutrophilic inflammation in the lamina propria of the mucosa, resulting in moderate separation of the bases large intestine glands (black asterisks). There is also marked expansion/thickening of the submucosa (vertical bars) with edema fluid that contains neutrophils. In contrast, in the ebselen-treated animals (C and D), there is milder neutrophilic inflammation in the mucosa without separation and crypts, as well as no or mild expansion/thickening of the submucosa (vertical bars) with edema and inflammation. H&E staining was used, and the images are at 200× magnification. The black bar represents 100 µM. Histopathological scores were determined (FIG. 4D) for vehicle- (circles) and ebselen- (squares) treated animals for inflammatory cell infiltration, submucosal edema, and mucosal hypertrophy. While none of the samples demonstrated signs of vascular or epithelial damage, the clinical scores for cell infiltration, submucosal edema and mucosal hypertrophy were significantly lower in the ebselen treated group (1.43±0.2) in comparison to the vehicle treated group (overall clinical score of 3.62±0.32). The mean of differences was 2.3, as seen in the plot of the overall average histopathological scores for ebselen- and vehicle-treated animals (FIG. 4E). Statistical analysis was performed using Mann-Whitney test. * indicates P<0.05, and ** indicates P<0.01.

Figure 6:
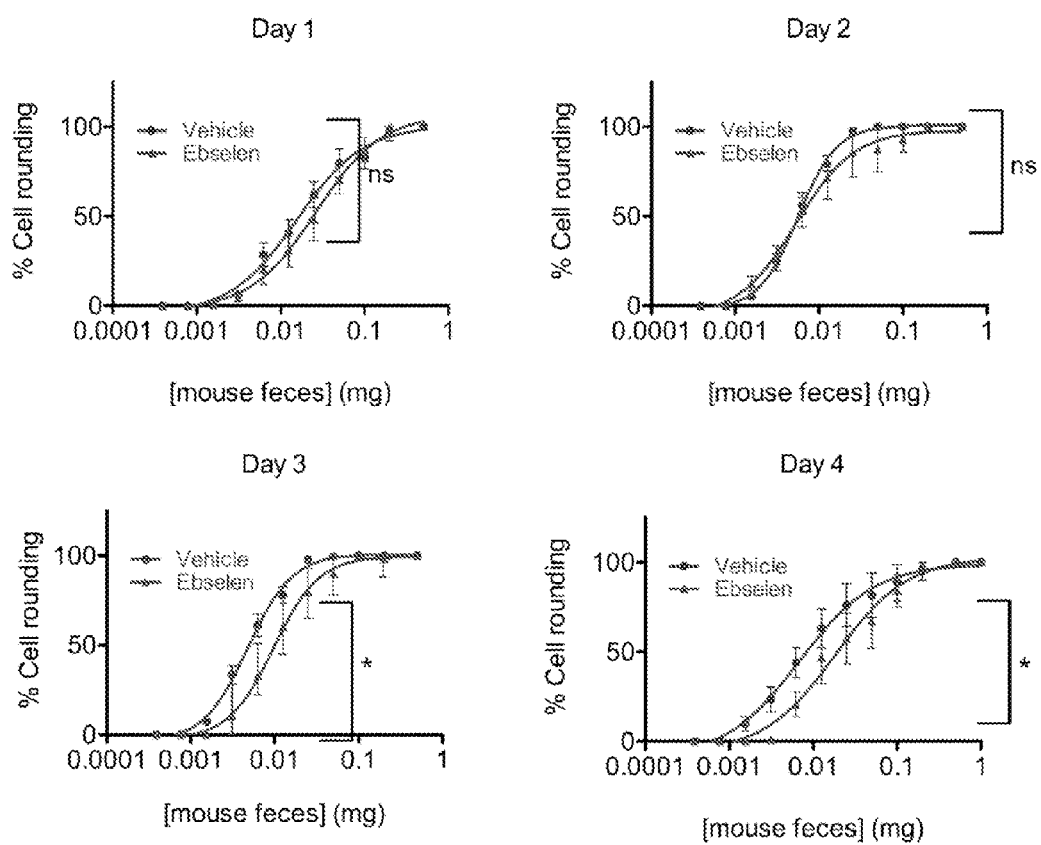
FIG. 6 consists of dose response plots showing the activity of TcdB toxin in feces of vehicle- and ebselen-treated mice throughout day 1-4 post C. difficile infection.

Dose response plots showing the activity of TcdB toxin in feces of vehicle- and ebselen-treated mice throughout day 1-4 post *C. difficile* infection are given in FIG. 6. The indicated µg of feces equivalents collected from *C. difficile*-infected mice treated with ebselen (triangles, n=8) or vehicle (circles, n=7) throughout days 1-4 were resuspended in PBS and applied to HFF cells. Cell rounding was calculated as the percentage of rounded cells relative to DMSO control treated cells. Results are mean±SEM. Samples were statistically analyzed using paired t test. ns=non-significant, *P<0.05, **P<0.01.

Figure 7:
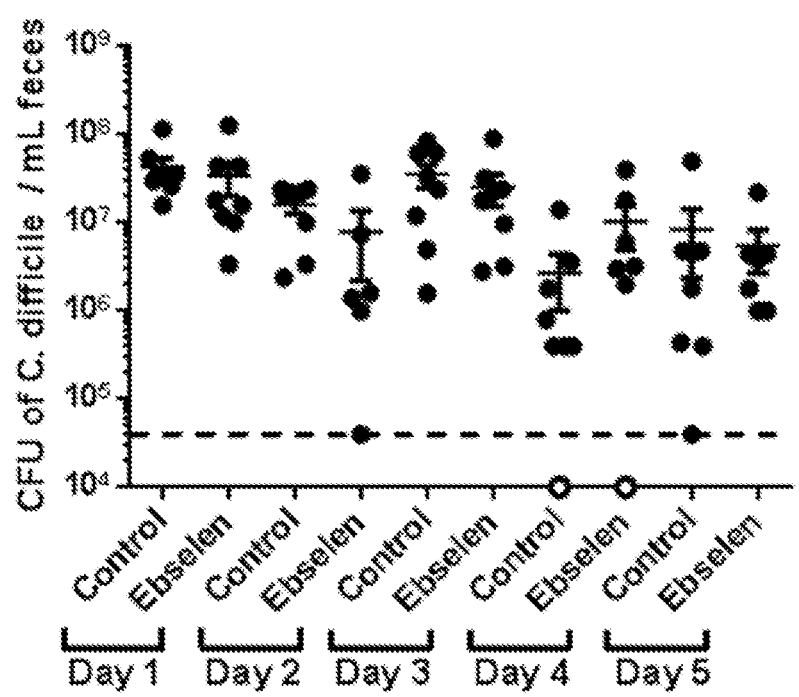
FIG. 7 is a plot showing lack of growth inhibitory or killing effect of ebselen on C. difficile.

Mice infected with *C. difficile* were treated with ebselen (200 mg/kg, once a day, via oral gavage) or vehicle. Serial dilutions of fecal homogenates at day 1-5 were prepared in sterile PBS and plated on CCFA plates, and *C. difficile* colony forming units (CFUs) were quantified (CFUs of *C. difficile* per ml of feces). No growth inhibitory or killing effect of ebselen on *C. difficile* was observed (FIG. 7).

Figure 8:
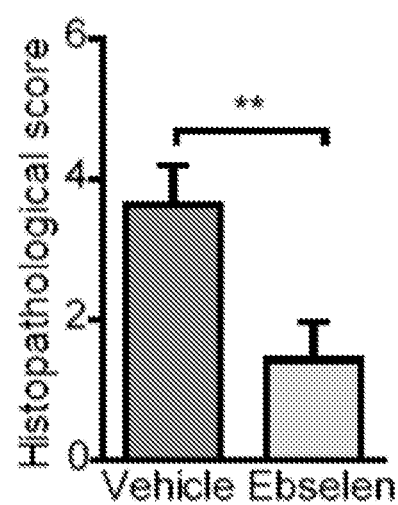
FIG. 8 is a bar graph showing histology analysis of the colon from mice infected with C. difficile.

As observed in photomicrographs of colon from mice infected with *Clostridium difficile*, there is moderate neutrophilic inflammation in the lamina propria of the mucosa, resulting in moderate separation of the bases large intestine glands (control group; data not shown). There is also marked expansion/thickening of the submucosa with edema fluid that contains neutrophils. In contrast, in ebselen treated animals, there is milder neutrophilic inflammation in the mucosa without separation and crypts, as well as no or mild expansion/thickening of the submucosa with edema and inflammation (ebselen group; data not shown). A bar graph summarizing a histology analysis of the colon from mice infected with *C. difficile* that were vehicle or ebselen treated is given in FIG. 8. The mice treated with ebselen showed significant improvement in overall pathology.

Example 5

Design a Colon-Specific Delivery System for 2-phenyl-1,2-benzoselenazol-3-one and Analogs Exemplified here are colon-specific formulations for optimum delivery of the drug with a relatively high local concentration, which may provide more effective therapy for CDI. CDI is a GI tract infection localized almost exclusively to colon. Delivery of the drugs to a specific site in the GI tract has several advantages: 1) much lower doses are required, reducing the possibility of adverse side effects; 2) treatment can be more effective as demonstrated in treatment of Crohn's disease and ulcerative colitis by a colon-specific drug olsalazine; 3) bioactive agent is less likely to be degraded or modified; and 4) drug can have much longer local residence. The rationale for treatment of CDI with a colon-specific formulation is that this will keep the compound at a high concentration within the region where the virulent factor resides. This will mitigate the main symptom of disease: watery diarrhea that is followed by stomach cramping and serious dehydration that can eventually lead to kidney failure, toxic megacolon, bowel perforation, and death.

The formulations include pH-dependent coating polymers for peroral delivery. Eudragit L100 and Eudragit S100 (Evonik Industries) are methacrylic acid copolymers, which dissolve at pH 6.0 and 7.0 respectively. The combination of these two polymers in various ratios makes it possible to manipulate drug release within the colonic 6.0-7.0 pH range. A defined combination of these polymers ensures that the release of drug from formulation occurs even when the pH value of the GI tract does not reach more than 6.8.

In one formulation, 2-phenyl-1,2-benzoselenazol-3-one or analogs will be entrapped into chitosan cores and Eudragit S100/Eudragit L100 using a spray drying method. Eudragit® S100 is a series of anionic copolymers based on methacrylic acid and methyl methacrylate, available from Evonik Industries AG, Rellinghauser Straβe 1-11, 45128 Essen, Germany. It is provided in powder form for release in the colon at pH 7.0.

Eudragit® L 100 is also a series of anionic copolymers based on methacrylic acid and methyl methacrylate. It is polymerized for dissolution above pH 6.0. Its targeted drug release area is the jejunum.

Tablets containing ebselen compounds can be coated using various combinations of two methacrylic acid copolymers, (Eudragit L100 and Eudragit 5100) by spraying from aqueous systems. Details of combinations can be found e.g. in Kahn et al., "A pH-dependent colon-targeted oral drug delivery system using methacrylic acid copolymers. II. Manipulation of drug release using Eudragit L100 and Eudragit 5100 combinations," Drug Dev Ind Pharm. 2000 May; 26(5):549-54.

Under conditions combining the appropriate polymers, no drug should be released at gastric pH. When the microspheres reach the colon a continuous release is predicted to take place for a period of 8-12 hours. The formulation may be adjusted to a final composition by testing in animals. For the purpose of colon-specific delivery testing, formulated drugs are dispersed in citric buffer (at pH=5 particles are stable) and administered to 25 Balb/c mice via oral gavage (200 μL final volume) at different doses (20, 40, 60 and 100 mg/kg-5 mice/dose). After 8 hours feces are collected, mice sacrificed, and colon resected for analysis of the drug content by liquid chromatography-mass spectrometry (LC-MS). Both colon-delivery formulated drug and non-formulated soluble analogs are used for the animal studies.

Another formulation using acrylate copolymers is described in "Methacrylic-based nanogels for the pH-sensitive delivery of 5-fluorouracil in the colon," Ashwanikumar N, et al., Int J Nanomedicine. 2012; 7:5769-79, Epub 2012 Nov. 15. Here, one prepares the ebselen compound with methacrylic-based copolymers known to demonstrate pH-sensitive swelling behavior and also form hydrogel matrices. The swelling of the hydrogel depends on the pH of the medium. In the case of methacrylic-based hydrogels, the swelling is observed between pH 7.2 and 7.8. Thus, in the colonic environment, they are assumed to exhibit a dynamic swelling behavior and sustained release of the entrapped drug molecules. Methacrylic acid (MA)-based hydrogels are believed to show considerable biocompatibility, as described previously.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

REFERENCES

1. Burke, K. E. & Lamont, J. T. Infection: A Worldwide Disease. *Gut Liver* 8, 1-6 (2014).
2. Puri, A. W. et al. Rational design of inhibitors and activity-based probes targeting *Clostridium difficile* virulence factor TcdB. *Chem. Biol.* 17, 1201-1211 (2010).
3. Ng, K. M. et al. Microbiota-liberated host sugars facilitate post-antibiotic expansion of enteric pathogens. *Nature* 502, 96-99 (2013).
4. Surawicz, C. M. et al. Guidelines for diagnosis, treatment, and prevention of *Clostridium difficile* infections. *Am. J. Gastroenterol.* 108, 478-98; quiz 499 (2013).
5. CDC, Morbidity and Mortality Weekly Report (MMWR) Mar. 9, 2012/61(09); 157-162.
6. R. Douglas Scott II. The Direct Medical Costs of Healthcare-Associated Infections in U.S. Hospitals and the Benefits of Prevention, Division of Healthcare Quality Promotion National Center for Preparedness, Detection, and Control of Infectious Diseases. Coordinating Center for Infectious Diseases. (2009).
7. Dubberke, E. R. & Olsen, M. A. Burden of *Clostridium difficile* on the healthcare system. *Clin. Infect. Dis.* 55 Suppl 2, S88-92 (2012).
8. Tran, M. C., Claros, M. C. & Goldstein, E. J. Therapy of *Clostridium difficile* infection: perspectives on a changing paradigm. *Expert Opin. Pharmacother.* 14, 2375-2386 (2013).
9. Kelly, C. P. Can we identify patients at high risk of recurrent *Clostridium difficile* infection? *Clin. Microbiol. Infect.* 18 Suppl 6, 21-27 (2012).
10. Hu, M. Y. et al. Prospective derivation and validation of a clinical prediction rule for recurrent *Clostridium difficile* infection. *Gastroenterology* 136, 1206-1214 (2009).
11. Walsh, C. in Antibiotics: actions, origins, resistance. (American Society for Microbiology (ASM), 2003).
12. Arias, C. A. & Murray, B. E. The rise of the *Enterococcus*: beyond vancomycin resistance. *Nat. Rev. Microbiol.* 10, 266-278 (2012).
13. Ramsey, A. M. & Zilberberg, M. D. Secular trends of hospitalization with vancomycin-resistant *enterococcus* infection in the United States, 2000-2006. *Infect. Control Hosp. Epidemiol.* 30, 184-186 (2009).

14. van Nood, E. et al. Duodenal infusion of donor feces for recurrent *Clostridium difficile*. *N. Engl. J. Med.* 368, 407-415 (2013).
15. Pamer, E. G. Fecal microbiota transplantation: effectiveness, complexities, and lingering concerns. *Mucosal Immunol.* 7, 210-214 (2014).
16. Vale, P. F., Fenton, A. & Brown, S. P. Limiting damage during infection: lessons from infection tolerance for novel therapeutics. *PLoS Biol.* 12, e1001769 (2014).
17. Taur, Y. & Pamer, E. G. Harnessing microbiota to kill a pathogen: Fixing the microbiota to treat *Clostridium difficile* infections. *Nat. Med.* 20, 246-247 (2014).
18. Shim, J. K., Johnson, S., Samore, M. H., Bliss, D. Z. & Gerding, D. N. Primary symptomless colonisation by *Clostridium difficile* and decreased risk of subsequent diarrhoea. *Lancet* 351, 633-636 (1998).
19. Kyne, L., Warny, M., Qamar, A. & Kelly, C. P. Asymptomatic Carriage of *Clostridium difficile* and Serum Levels of IgG Antibody against Toxin A. *N. Engl. J. Med.* 342, 390-397 (2000).
20. O'Connor, J. R., Johnson, S. & Gerding, D. N. *Clostridium difficile* infection caused by the epidemic BI/NAP1/027 strain. *Gastroenterology* 136, 1913-1924 (2009).
21. Lyras, D. et al. Toxin B is essential for virulence of *Clostridium difficile*. *Nature* 458, 1176-1179 (2009).
22. Pruitt, R. N. & Lacy, D. B. Toward a structural understanding of *Clostridium difficile* toxins A and B. *Front. Cell. Infect. Microbiol.* 2, 28 (2012).
23. Shen, A. et al. Defining an allosteric circuit in the cysteine protease domain of *Clostridium difficile* toxins. *Nat. Struct. Mol. Biol.* 18, 364-371 (2011).
24. Chumbler, N. M. et al. *Clostridium difficile* Toxin B causes epithelial cell necrosis through an autoprocessing-independent mechanism. *PLoS Pathog.* 8, e1003072 (2012).
25. Farrow, M. A. et al. *Clostridium difficile* toxin B-induced necrosis is mediated by the host epithelial cell NADPH oxidase complex. *Proc. Natl. Acad. Sci. U.S.A.* 110, 18674-18679 (2013).
26. Feltis, B. A. et al. *Clostridium difficile* toxins A and B can alter epithelial permeability and promote bacterial paracellular migration through HT-29 enterocytes. *Shock* 14, 629-634 (2000).
27. Eaton, S. R. & Mazuski, J. E. Overview of severe *Clostridium difficile* infection. *Crit. Care Clin.* 29, 827-839 (2013).
28. Bhabak, K. P. & Mugesh, G. Functional mimics of glutathione peroxidase: bioinspired synthetic antioxidants. *Acc. Chem. Res.* 43, 1408-1419 (2010).
29. Yamaguchi, T. et al. Ebselen in acute ischemic stroke: a placebo-controlled, double-blind clinical trial. Ebselen Study Group. *Stroke* 29, 12-17 (1998).
30. Favrot, L. et al. Mechanism of inhibition of *Mycobacterium tuberculosis* antigen 85 by ebselen. *Nat. Commun.* 4, 2748 (2013).
31. Lieberman, O. J., Orr, M. W., Wang, Y. & Lee, V. T. High-throughput screening using the differential radial capillary action of ligand assay identifies ebselen as an inhibitor of diguanylate cyclases. *ACS Chem. Biol.* 9, 183-192 (2014).
32. Wust, J., Sullivan, N. M., Hardegger, U. & Wilkins, T. D. Investigation of an outbreak of antibiotic-associated colitis by various typing methods. *J. Clin. Microbiol.* 16, 1096-1101 (1982).
33. Pawlowski, S. W. et al. Murine model of *Clostridium difficile* infection with aged gnotobiotic C57BL/6 mice and a BI/NAP1 strain. *J. Infect. Dis.* 202, 1708-1712 (2010).
34. Yang, G. et al. Expression of recombinant *Clostridium difficile* toxin A and B in *Bacillus megaterium*. *BMC Microbiol.* 8, 192-2180-8-192 (2008).
35. Lanis, J. M., Heinlen, L. D., James, J. A. & Ballard, J. D. *Clostridium difficile* 027/BI/NAP1 encodes a hypertoxic and antigenically variable form of TcdB. *PLoS Pathog.* 9, e1003523 (2013).

What is claimed is:

1. A method of inhibiting a *Clostridium difficile* toxin which is at least one of TcdB and TcdA in a subject suspected of having a *Clostridium difficile* infection, comprising administering to the subject suspected of having a *Clostridium difficile* infection an effective amount of a composition comprising ebselen:

to inhibit the *Clostridium difficile* toxin in the subject.

2. The method of claim 1, further comprising administering to the subject at least one antibiotic.

3. The method of claim 1, wherein the administering is by oral administration.

4. The method of claim 3, wherein the oral administration comprises administering an oral formulation for release in the colon.

5. The method of claim 3, wherein the oral administration comprises administering an oral formulation for release at a pH of from 6.0 to 7.0.

6. The method of claim 1, wherein the composition comprising ebselen further comprises a colon-retentive formulation.

7. The method of claim 1, wherein the composition comprising ebselen comprises ebselen entrapped in chitosan cores and anionic copolymers based on methacrylic acid and methyl methacrylate.

8. The method of claim 1, wherein the composition comprising ebselen comprises a coating containing two or more enteric materials surrounding a core of ebselen.

9. The method of claim 2, wherein the at least one antibiotic is selected from the group consisting of: metronidazole, fidaxomicin, vancomycin, and combinations thereof.

* * * * *